United States Patent
Morris

(10) Patent No.: US 7,022,116 B2
(45) Date of Patent: Apr. 4, 2006

(54) METHOD FOR MONITORING BOLUS DELIVERY

(75) Inventor: Mary M. Morris, Mounds View, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 10/691,814

(22) Filed: Oct. 23, 2003

(65) Prior Publication Data

US 2005/0090799 A1    Apr. 28, 2005

(51) Int. Cl.
    *A61M 31/00*    (2006.01)
(52) U.S. Cl. ...................................... 604/508
(58) Field of Classification Search ............ 604/65–67, 604/500, 507, 508, 509, 510, 511, 512, 513; 128/DIG. 12, DIG. 13
    See application file for complete search history.

(56) References Cited

U.S. PATENT DOCUMENTS

| | | | |
|---|---|---|---|
| 4,898,576 A | * | 2/1990 | Philip .......................... 604/505 |
| 5,006,997 A | | 4/1991 | Reich .......................... 364/510 |
| 5,190,522 A | * | 3/1993 | Wojcicki et al. .............. 604/65 |
| 5,279,544 A | | 1/1994 | Gross et al. ................... 604/20 |
| 5,342,298 A | | 8/1994 | Michaels et al. .............. 604/65 |
| 5,605,545 A | | 2/1997 | Nowosielski et al. ........ 604/118 |
| 5,713,923 A | * | 2/1998 | Ward et al. ..................... 607/3 |
| 5,893,838 A | | 4/1999 | Daoud et al. .................. 604/26 |
| 5,899,873 A | | 5/1999 | Jones et al. ..................... 604/4 |
| 5,928,195 A | | 7/1999 | Malamud et al. ........... 604/141 |
| 6,203,523 B1 | | 3/2001 | Haller et al. .............. 604/93.01 |

* cited by examiner

Primary Examiner—Manuel Mendez

(57) ABSTRACT

A method for monitoring a bolus delivered to a pressure-responsive valve of a fluid infusion catheter includes delivering the bolus through the infusion catheter over a period of time lasting between approximately one minute and approximately 60 minutes and observing a measured pressure versus time during the bolus delivery.

14 Claims, 5 Drawing Sheets

US 7,022,116 B2

METHOD FOR MONITORING BOLUS DELIVERY

TECHNICAL FIELD

The present invention relates to the field of implantable drug infusion devices and more particularly to a method for monitoring boluses delivered by an implantable drug infusion device through an infusion catheter.

BACKGROUND

Implantable drug infusion devices are used to provide patients with programmable long-term dosage or infusion of a drug or any other therapeutic agent. These devices typically include a pump and a catheter attached to the pump and extending to a target site through which boluses of infusate are delivered. It is desirable to monitor such devices to verify bolus delivery or to identify causes of unsuccessful bolus delivery, such as leakage or occlusion.

BRIEF DESCRIPTION OF THE DRAWINGS

The following drawings are illustrative of particular embodiments of the invention and therefore do not limit its scope, but are presented to assist in providing a proper understanding of the invention. The drawings are not to scale (unless so stated) and are intended for use in conjunction with the explanations in the following detailed description. The present invention will hereinafter be described in conjunction with the appended drawings, wherein like numerals denote like elements, and.

DETAILED DESCRIPTION OF THE DRAWINGS

The following detailed description is exemplary in nature and is not intended to limit the scope, applicability, or configuration of the invention in any way. Rather, the following description provides a practical illustration for implementing exemplary embodiments of the invention.

Figure 1:
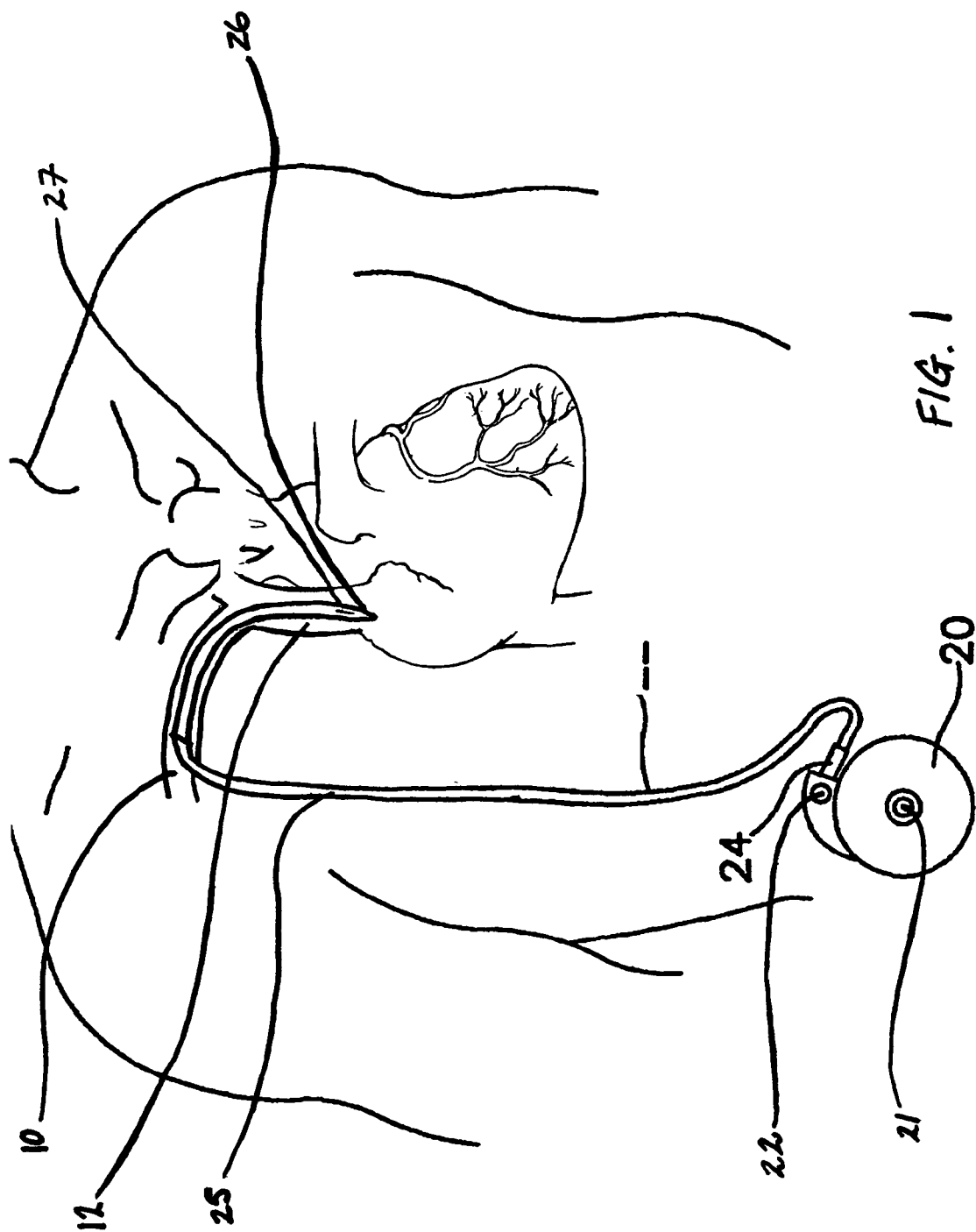
FIG. 1 is a schematic diagram of an implanted drug infusion device wherein embodiments of the present invention may be practiced.

FIG. 1 is a schematic diagram of an implanted drug infusion device wherein embodiments of the present invention may be practiced. FIG. 1 illustrates the device including a pump 20, implanted in an abdominal region of a patient, and an infusion catheter 25, coupled to pump 20 via a connector 24, extending into a superior vena cava 12 via a subclavian vein 10. FIG. 1 further illustrates catheter 25 including a valve 27 positioned in proximity to a distal end 26; valve 27 may be any type of valve known to those skilled in the art, for example a slit valve, a sleeve valve or a small hole valve. Pump 20 includes a reservoir, which may be refilled via an injection port 21, and a peristaltic pump, which propel a bolus of infusate out from the reservoir through catheter 25; an example of such a pump is the Medtronic SynchroMed™. Bolus volumes according to embodiments of the present invention may range between approximately 0.05 mL and approximately 1 mL and delivery times may range between approximately 1 minute and approximately 60 minutes.

According to one embodiment of the present invention, as illustrated in FIG. 1, pump 20 further includes a catheter port 22 through which a physician may insert a needle coupled to an external pressure transducer to monitor intra-catheter pressure versus time as a bolus of infusate is delivered through catheter 25; such means to monitor pressure are well known to those skilled in the art. Alternately a pressure transducer may be built into pump 20 or catheter connector 24 to measure the intra-catheter pressure. Analysis of the intra-catheter pressure versus time during bolus delivery can be used to verify successful bolus delivery or to diagnose problems with the implantable infusion device, which prevent successful bolus delivery.

Figure 2:
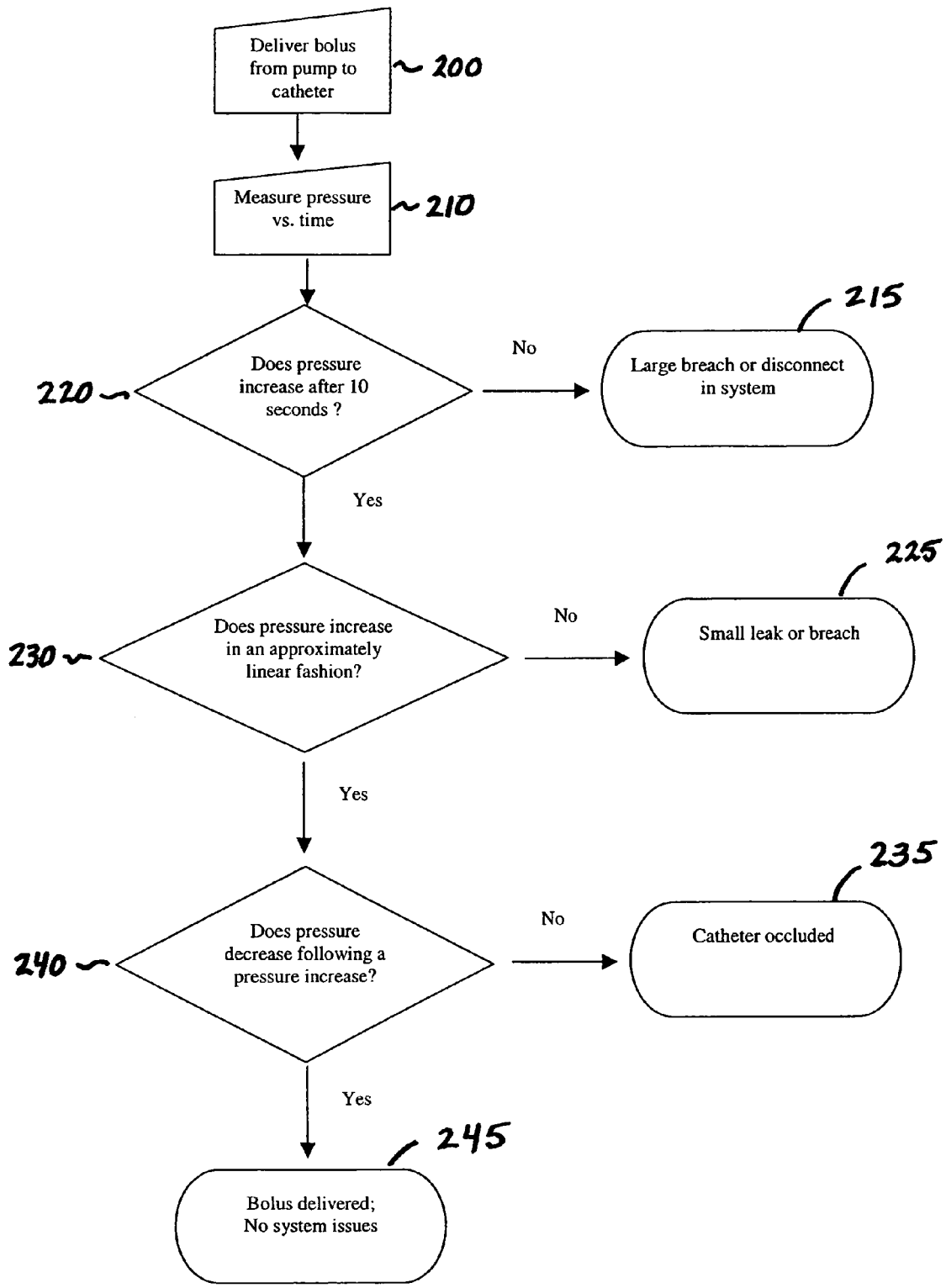
FIG. 2 is a flowchart detailing a method according to one embodiment of the present invention.

FIG. 2 is a flowchart detailing a method according to one embodiment of the present invention wherein a measured pressure versus time is analyzed. FIG. 1 illustrates a first step 200 of delivering a bolus from a pump to a catheter and a second step 210 of measuring intra-catheter pressure versus time as the bolus is being delivered. Initial analysis of the measured pressure versus time determines if pressure has increased after the first 10 seconds of bolus delivery, 220; if pressure has not increased, the method infers that there is a large breach or disconnect in the device, 215, but if pressure has increased a next analysis step, 230, is performed. At step 230, the method analyzes the pressure increase versus time to determine if it is approximately linear; if the measured pressure increase is non-linear, the method infers that there is a small leak or breach in the catheter, 225, but if the increase is approximately linear, a next analysis step, 240, is performed. At step 240, the method analyzes the measured pressure versus time to determine if a pressure decrease follows the pressure increase; if the pressure continues to rise, the method infers that the catheter is occluded, 235, while, if the pressure rises and then falls, the method infers that the bolus has been successfully delivered, 245. Methods according to some embodiments of the present invention include controls to abort bolus delivery at any of the inference points 215, 225 or 235.

EXAMPLES

Figure 3A:
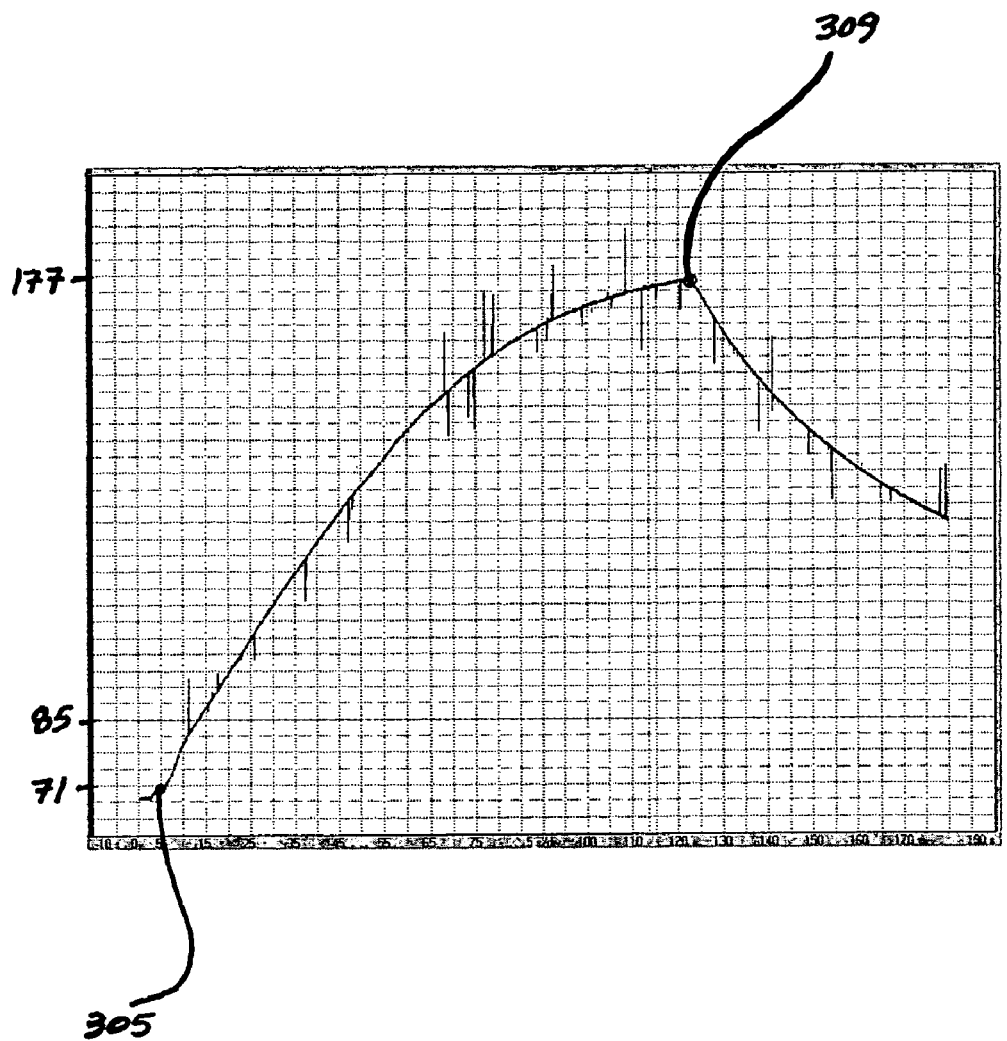
FIG. 3A is a plot of pressure versus time measured during a bolus delivery in leaky device.
Figure 3B:
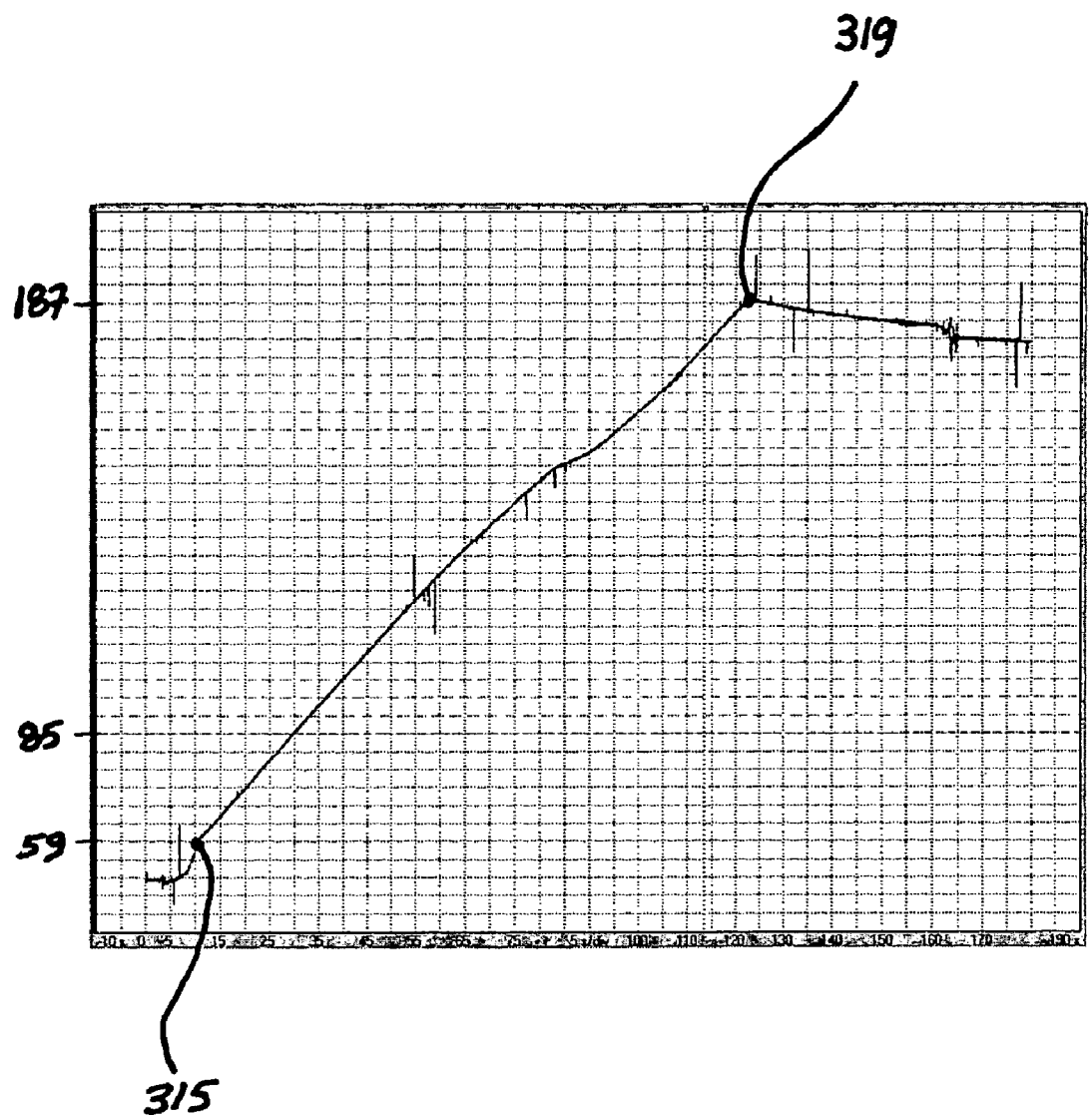
FIG. 3B is a plot of pressure versus time measured during a bolus delivery in an occluded device.
Figure 3C:
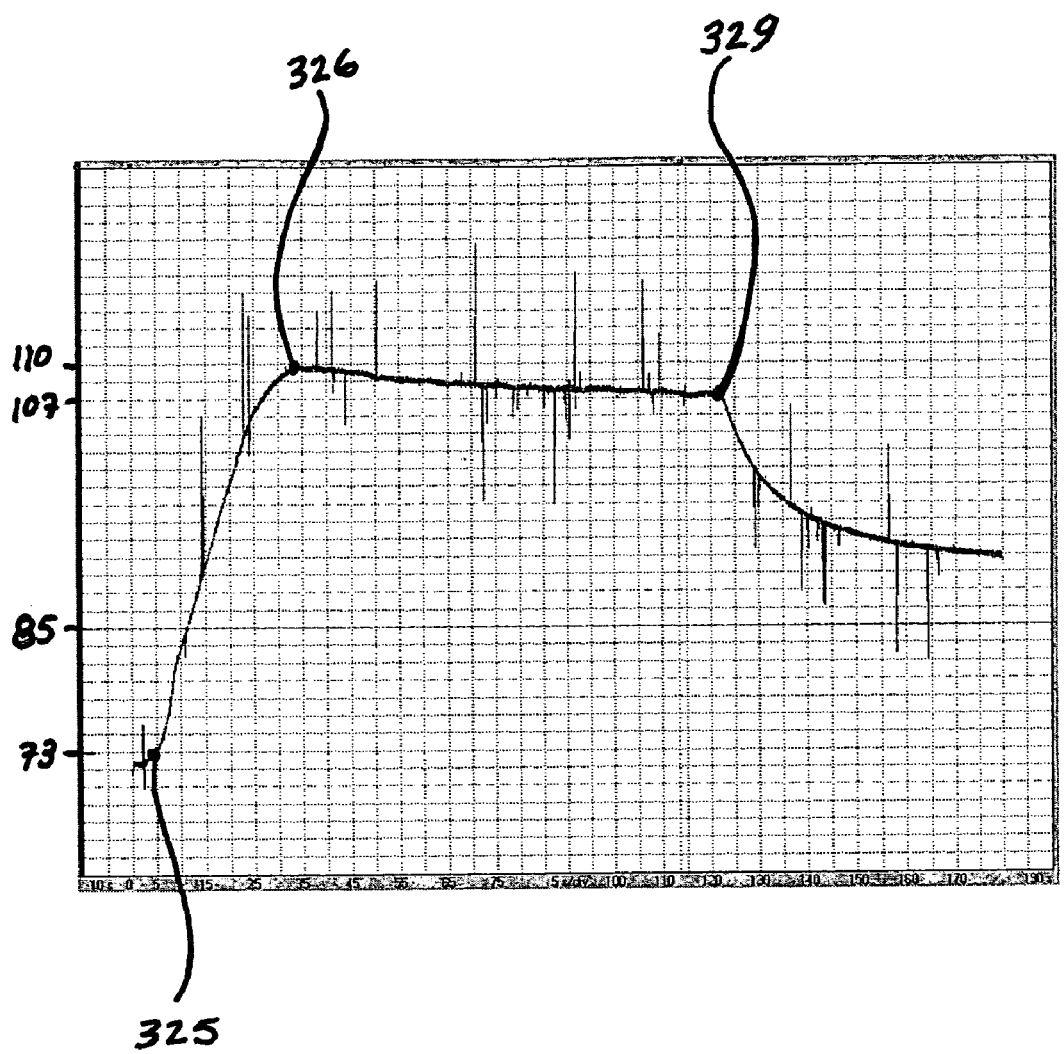
FIG. 3C is a plot of pressure versus time measured during a successful bolus injection.

FIGS. 3A–C present plots of pressure in mmHg (ordinate) versus time in seconds (abscissa) collected via an external transducer coupled to a needle inserted within catheter ports, i.e. port 22 shown in FIG. 1, of exemplary devices. Each device included a valved infusion catheter implanted within a venous system.

FIG. 3A is a plot of pressure versus time measured during a bolus delivery from a pump through an infusion catheter including a sleeve valve wherein there was a leak at a coupling between the catheter and the pump. FIG. 3A illustrates a non-linear increase in pressure, from approximately 71 mmHg to approximately 177 mmHg, in between a pump start point 305 and a pump stop point 309 and corresponds to inference point 225 presented in FIG. 2.

FIG. 3B is a plot of pressure versus time measured during a bolus delivery from a pump through an infusion catheter, including a small hole valve, wherein the catheter was occluded by thrombus. FIG. 3B illustrates a rise in pressure, from approximately 59 mmHg to approximately 187 mmHg, between a pump start point 315 and a pump stop point 319 and corresponds to inference point 235 presented in FIG. 2.

FIG. 3C is a plot of pressure versus time measured during a successful bolus injection from a pump through a catheter including a slit valve. FIG. 3C illustrates an approximately linear pressure increase between pump start point 325 (~73 mmHg) and a maximum pressure point 326 (~110 mmHg at ~30–35 seconds) and then a decrease in pressure from point 326 to pump stop point 329 (~107 mmHg); FIG. 3C corresponds to inference point 245 presented in FIG. 2.

In the foregoing detailed description, the invention has been described with reference to specific embodiments. However, it may be appreciated that various modifications and changes can be made without departing from the scope of the invention as set forth in the appended claims.

I claim:

1. A method for monitoring a bolus delivered from a pump to a fluid infusion catheter, comprising the steps of:
    delivering the bolus to the infusion catheter over a period of time lasting between approximately one minute and approximately 60 minutes; and
    observing a measured intra-catheter pressure versus time during the bolus delivery, wherein observation is made as to whether the measured pressure initially increases at an approximately linear rate followed by a decrease in measured pressure.

2. The method of claim 1, wherein the period of time is between approximately 1 minute and 3 minutes.

3. The method of claim 1, wherein a volume of the bolus is between approximately 0.05 mL and approximately 1 mL.

4. The method of claim 3, wherein the volume is between approximately 0.1 mL and approximately 0.25 mL.

5. The method of claim 1, further comprising the step of inferring a successful bolus delivery based on an observed decrease in the pressure following an observed increase in the pressure during the bolus delivery.

6. The method of claim 1, further comprising the step of inferring a leak in the infusion catheter based on an observed non-linear increase in the pressure during the bolus delivery.

7. The method of claim 1, further comprising the step of inferring a leak in the infusion catheter, proximal to the valve, based on an observed pressure which does not increase within approximately 10 seconds from a start of the bolus delivery.

8. The method of claim 1, further comprising the step of inferring an occlusion of the infusion catheter based on no observed pressure decrease following an observed pressure increase, during the bolus delivery.

9. A method for controlling a bolus delivered to a pressure-responsive valve of a fluid infusion catheter, comprising the steps of:
    delivering the bolus through the infusion catheter over a period of time lasting between approximately 1 minute and approximately 60 minutes;
    monitoring intra-catheter pressure versus time during the bolus delivery; and
    aborting the bolus delivery if the pressure versus time does not conform to a predetermined pattern of pressure change over time.

10. The method of claim 9, wherein the predetermined pattern includes an approximately linear increase in the pressure versus time.

11. The method of claim 9, wherein the predetermined pattern includes an increase in the pressure and then a decrease in the pressure after approximately 50 seconds from a start of the bolus delivery.

12. The method of claim 9, wherein the period of time is between approximately 1 minute and approximately 3 minutes.

13. The method of claim 9, wherein a volume of the bolus is between approximately 0.05 mL and approximately 1 mL.

14. The method of claim 13, wherein the volume is between approximately 0.1 mL and approximately 0.25 mL.

* * * * *